US012797108B2

(12) United States Patent
Simovich et al.

(10) Patent No.: US 12,797,108 B2
(45) Date of Patent: Nov. 17, 2026

(54) LAPAROSCOPIC INCISION WIDENER

(71) Applicant: Human Art Devices LLC, Aventura, FL (US)

(72) Inventors: Guillermo David Simovich, Aventura, FL (US); Michael Yuzefovich, Aventura, FL (US)

(73) Assignee: Human Art Devices LLC, Aventura, FL (US)

( * ) Notice: Subject to any disclaimer, the term of this patent is extended or adjusted under 35 U.S.C. 154(b) by 0 days.

(21) Appl. No.: 19/257,084

(22) Filed: Jul. 1, 2025

(65) Prior Publication Data

US 2026/0000428 A1 Jan. 1, 2026

Related U.S. Application Data

(60) Provisional application No. 63/732,639, filed on Sep. 9, 2024, provisional application No. 63/732,605, filed on Sep. 3, 2024, provisional application No. 63/732,227, filed on Jul. 26, 2024, provisional application No. 63/731,995, filed on Jul. 1, 2024.

(51) Int. Cl.

| | |
|---|---|
| ***A61B 17/32*** | (2006.01) |
| ***A61B 17/34*** | (2006.01) |
| *A61B 1/313* | (2006.01) |
| *A61B 17/00* | (2006.01) |

(52) U.S. Cl.

CPC .. *A61B 17/3415* (2013.01); *A61B 17/320016* (2013.01); *A61B 1/3132* (2013.01); *A61B 2017/00398* (2013.01)

(58) Field of Classification Search

CPC ........ A61B 17/3415; A61B 17/320016; A61B 17/3209; A61B 1/3132; A61B 2017/00398

See application file for complete search history.

(56) References Cited

U.S. PATENT DOCUMENTS

| | | | | |
|---|---|---|---|---|
| 5,372,588 | A | 12/1994 | Farley et al. | |
| 5,817,119 | A * | 10/1998 | Klieman | A61B 34/71 606/174 |
| 6,159,200 | A | 12/2000 | Verdura et al. | |
| 7,060,077 | B2 * | 6/2006 | Gordon | A61B 17/0469 606/139 |
| 7,766,937 | B2 | 8/2010 | Ravikumar | |
| 8,225,798 | B2 | 7/2012 | Baldwin et al. | |
| 8,747,407 | B2 | 6/2014 | Gorek | |

(Continued)

FOREIGN PATENT DOCUMENTS

CN 116807566 A 9/2023

OTHER PUBLICATIONS

International Search Report and Written Opinion for corresponding International Application No. PCT/US2025/036117, dated Aug. 29, 2025, 13 pages.

*Primary Examiner* — Christina C Lauer

(74) *Attorney, Agent, or Firm* — Leech Tishman Fuscaldo & Lampl, LLC

(57) ABSTRACT

A surgical instrument for insertion through a laparoscopic trocar, the instrument having an elongated tubular body and a blade deployment assembly associated with the tubular body. One or more blades are coupled to the deployment assembly and movable between a retracted position within a diameter defined by the tubular body and an extended position projecting radially or outward from the tubular body.

7 Claims, 9 Drawing Sheets

(56) References Cited

U.S. PATENT DOCUMENTS

| | | | |
|---|---|---|---|
| 8,932,210 B2 | 1/2015 | Woods | |
| 9,168,051 B2 | 10/2015 | Weisenburgh, II et al. | |
| 9,198,635 B2 | 12/2015 | Crum et al. | |
| 2003/0171764 A1* | 9/2003 | Debbas | A61B 17/0057 606/222 |
| 2010/0228182 A1* | 9/2010 | Clark, III | A61B 18/20 606/171 |
| 2013/0310869 A1 | 11/2013 | Crenshaw et al. | |
| 2014/0171919 A1* | 6/2014 | Blacker | A61B 34/30 604/533 |
| 2014/0350576 A1* | 11/2014 | Patel | A61B 17/0491 606/145 |
| 2015/0216514 A1* | 8/2015 | Weisbrod | A61B 17/0057 606/232 |
| 2019/0105062 A1 | 4/2019 | Tally et al. | |
| 2022/0354526 A1 | 11/2022 | Mirza | |

* cited by examiner

LAPAROSCOPIC INCISION WIDENER

CROSS-REFERENCE TO RELATED APPLICATION

This application claims the benefit of U.S. Provisional Application Ser. No. 63/732,639 filed Sep. 9, 2024, and claims the benefit of U.S. Provisional Application Ser. No. 63/732,605, filed Sep. 3, 2024, and claims the benefit of U.S. Provisional Application Ser. No. 63/732,227, filed Jul. 26, 2024, and claims the benefit of U.S. Provisional Application Ser. No. 63/731,995, filed Jul. 1, 2024.

FIELD

The present invention relates to surgical instruments, and more particularly to a laparoscopic incision extending device having a cutting blades and a blade deployment mechanism for controlled enlargement of trocar incisions.

BACKGROUND

Laparoscopy has revolutionized modern surgery and has become the standard first-line surgical approach for a wide variety of diseases affecting the abdomen and pelvis. This minimally invasive surgical technique has gained broad acceptance in many medical specialties due to its significant advantages over traditional open surgical procedures, including reduced patient trauma, shorter recovery times, decreased postoperative pain, minimal scarring, and reduced risk of complications such as infection and adhesion formation.

Contemporary laparoscopic procedures use commercially available trocars that typically range from 5 to 15 millimeters in diameter. These trocars are employed in both conventional laparoscopic platforms and state-of-the-art robotic surgical systems. The trocar serves as a portal through which surgeons insert various instruments, cameras, and other necessary equipment to perform complex surgical procedures within the confined space of the body cavity. The small size of these access ports is one of the key advantages of laparoscopic surgery, as it minimizes the trauma to the abdominal wall and surrounding tissues.

However, despite the numerous advantages of laparoscopic surgery, surgeons consistently encounter a universal and persistent problem that has plagued the field since its inception. This challenge arises when attempting to remove masses, specimens, or organs that are significantly greater in size than the diameter of the trocar through which they were accessed during the surgical procedure. This size mismatch creates a fundamental dilemma that forces surgeons to make difficult decisions regarding specimen removal while balancing patient safety, procedural efficiency, and optimal outcomes.

The problem of specimen extraction through small laparoscopic ports is not limited to a single surgical specialty but is a common issue experienced across multiple disciplines including general surgery, obstetrics and gynecology, urology, thoracic surgery, and other specialized fields. For example, in general surgery, surgeons frequently encounter this challenge when removing gallbladders containing large stones, portions of bowel, or tumors that have been resected laparoscopically. Gynecologic surgeons face similar difficulties when extracting enlarged ovaries, uterine specimens, or masses that were addressed through laparoscopic approaches. Similarly, urologists encounter problems when removing kidney specimens, large stones, or tissue masses through small laparoscopic ports.

When dealing with large masses, surgeons are often forced to resort to non-standard and improvised techniques that carry significant risks and potential complications. The most common approach involves blindly transecting the skin, fascia, and peritoneum using conventional surgical instruments not intended for this purpose. This approach lacks precision, control, and predictability, leading to several serious concerns that compromise both the immediate procedure and long-term patient outcomes.

The risks associated with improvised incision enlargement techniques are numerous and potentially severe. Bowel injury represents one of the most serious complications, as the blind cutting approach may inadvertently damage intestinal structures that have migrated into the surgical field. Fascial dehiscence is another significant concern, as uncontrolled cutting may create irregular or excessive fascial defects that compromise the integrity of the abdominal wall and potentially lead to hernia formation. Specimen retrieval or catch bag (also known as endo catch or endo bag) puncture is a particularly frustrating complication that can result in specimen spillage within the peritoneal cavity, potentially leading to contamination or the need for extensive irrigation and cleanup procedures.

Subcutaneous hematoma formation is another common complication resulting from uncontrolled tissue trauma during improvised incision enlargement. These hematomas can cause significant postoperative discomfort, delayed healing, and aesthetic concerns for patients. Perhaps most notably from a patient satisfaction perspective, cosmetic asymmetry of the skin frequently results from irregular or uneven incision enlargement, leading to poor aesthetic outcomes that can cause long-term patient dissatisfaction and potentially require additional corrective procedures.

The struggle to remove large masses from small laparoscopic port sites has evolved into one of the most time-consuming and frustrating steps of many laparoscopic procedures. This challenge often transforms what should be a straightforward specimen extraction into a prolonged and stressful portion of the operation, leading to increased operative times, elevated surgeon frustration levels, and potential patient safety concerns. The extended operative time required for improvised incision enlargement not only increases the overall cost of the procedure but also extends the patient's exposure to anesthesia and increases the risk of complications associated with prolonged surgical procedures.

The unique requirements of laparoscopic surgery create many engineering challenges. For example, laparoscopic devices must be capable of insertion through narrow trocar channels typically measuring between 5 and 15 millimeters in diameter, requiring precise dimensional control and specialized geometries. The devices must navigate through multiple tissue layers including skin, subcutaneous tissue, fascial planes, and peritoneum, each with different mechanical properties and cutting requirements. Operation within insufflated body cavities under pneumoperitoneum creates additional challenges related to pressure maintenance, gas leakage prevention, and compatibility with carbon dioxide insufflation systems.

Withdrawal cutting or extension through a full-thickness abdominal wall represents a unique challenge not present in superficial applications. The device must maintain cutting efficiency and control while being withdrawn through tissues of varying thickness and density. Compatibility with laparoscopic visualization systems is essential, as surgeons must maintain clear visual monitoring of the procedure through standard laparoscopic cameras and lighting systems. The need for sterile deployment within internal body cavities creates additional requirements for biocompatibility, sterilization compatibility, and contamination prevention.

SUMMARY

The present invention addresses the aforementioned limitations and challenges with a surgical instrument called a laparoscopic incision extender. The incision extender can include deployment mechanisms for cutting blades that are optimized for specific surgical situations, surgeon preferences, and procedural requirements.

The surgical instrument includes a tube or housing that is narrow enough to pass through a trocar; a deployment assembly at least partially disposed within the tube; and at least one cutting blade coupled to the deployment assembly and movable between a retracted position within a perimeter diameter defined by the tube body and an extended position projecting beyond the perimeter.

The deployment assembly comprises can include a motor disposed in a housing at a first end of the tube; a first pulley mechanically connected to the motor; a second pulley proximate a second end of the tube; a flexible belt extending longitudinally through the tube from the first pulley to the second pulley; and the at least one cutting blade coupled to the second pulley, wherein rotation of the first pulley causes movement of the flexible belt to rotate the second pulley, and wherein movement of the second pulley causes extension and retraction of the at least one cutting blade.

The deployment assembly can also include manually operable handles located at a proximal end of the instrument; and a mechanical linkage connecting the handles to the at least one cutting blade, wherein movement of the manually operable handles causes extension and retraction of the at least one cutting blade.

The deployment assembly can further include a rod disposed longitudinally within the tube; and a pivoting linkage connecting the rod to the at least one cutting blade, wherein rotation of the rod causes extension and retraction of the at least one cutting blade.

A method of expanding a laparoscopic incision using the surgical instrument includes inserting a device as described above through a trocar that has been placed within the body through an incision created to introduce the trocar, such that the cutting blades are positioned within the body cavity beyond multiple tissue layers; and actuating the deployment mechanism to pivot the cutting blades from a retracted to an extended position while maintaining laparoscopic visualization within the body cavity. The blades are maintained in an extended position with the cutting edges of the blades facing the exterior of the body. The instrument and the trocar are simultaneously removed from the body while the blades are extended to cut through peritoneum, fascia, and skin to enlarge the original incision made for introduction of the trocar.

In some embodiments, the device is provided as a kit or modular system in which the user may select an appropriate size tube for use with a selected trocar, and one of a motorized belt mechanism, spring-actuated mechanism, or threaded rod system depending on procedural requirements. These mechanisms may be interchangeable within a reusable or disposable housing.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

A laparoscopic incision extender of the present invention addresses longstanding challenges of specimen extraction in minimally invasive surgery by providing one or more cutting blades that can be deployed beyond the periphery of a trocar to permit precise, controlled tissue cutting to extend/enlarge an incision originally made for introduction of the trocar into the body. The enlarged incision allows for intact removal of masses larger in diameter than the trocar.

As described below with reference to the figures, an exemplary device for extending laparoscopic incisions includes an elongated tube configured for insertion through a casing tube of a laparoscopic trocar. Thus, “trocar” and “casing tube” can be used interchangeably when referring to placement of the elongated tube. Common trocars/casing tubes have an inner diameter between 5 and 15 millimeters, and the tube therefore has a smaller diameter that can range from just under 5 to 15 millimeters. Thus, a slightly less than 10 mm tube would be casing tube that is 10 mm (5 with 5, and 15 with 15). A cutting blade deployment mechanism is provided to increase and decrease the distance one or more cutting blades extend from the periphery or circumferential edge of the trocar. Exemplary cutting blade deployment mechanisms are shown that can include a motor-driven belt system, a spring-loaded manual system, and a threaded rod retractor system to retract and extend the cutting blade(s). A positioning element can be provided to maintain alignment of the device within the trocar during insertion and operation. The device can extend a trocar incision through at least three tissue layers including skin, fascia, and peritoneum during controlled withdrawal of the device and trocar.

Figure 1:
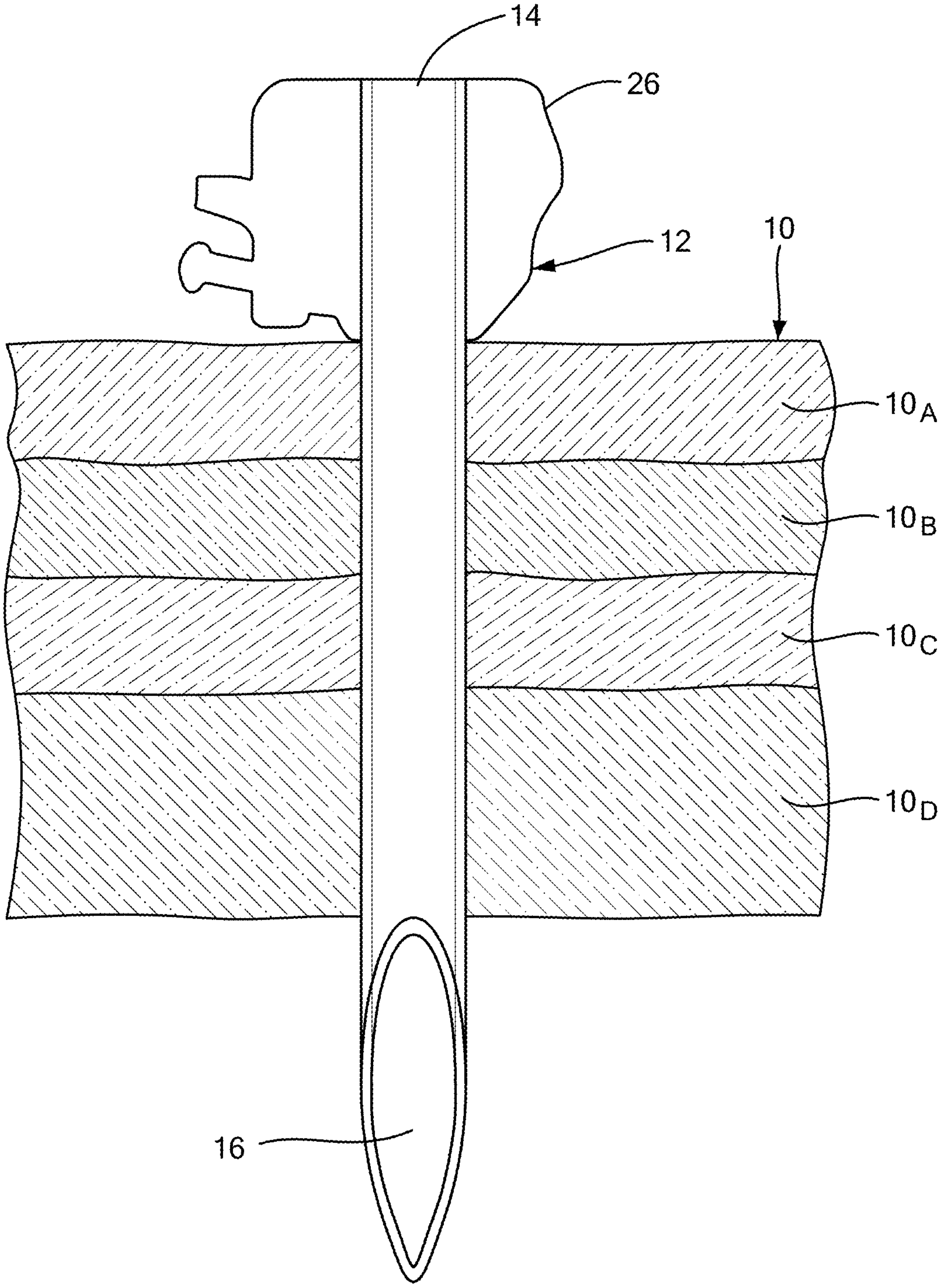
FIG. 1 is a sectional view of an abdominal wall showing a trocar having been passed through the abdominal wall.

Referring now to FIG. 1, a side sectional view of an abdominal wall 10 is shown with a trocar 12 placed through the abdominal wall. The abdominal will is comprised of many layers of tissue such as skin, superficial fat, deep membranous layer, investing facia, muscles, and parietal peritoneum. These layers are shown schematically as 10*a*,

10*b*, 10*c*, and 10*d*. The trocar includes an open proximal end 14 that is outside the body and an open distal end 16 that is positioned to access a space within the abdominal cavity. The trocar provides a passage from a point exterior to the body (abdomen) to a point interior the body, from the proximal end 14 to the distal end 16, through which objects and instruments may be passed. It will be noted that the distal end 16 can be cut at an angle and sharp like a syringe needle so that it can readily pierce tissue. However, a casing tube can have a flat end as well. The shape of end of the trocar/casing tube is not limiting.

Figure 2:
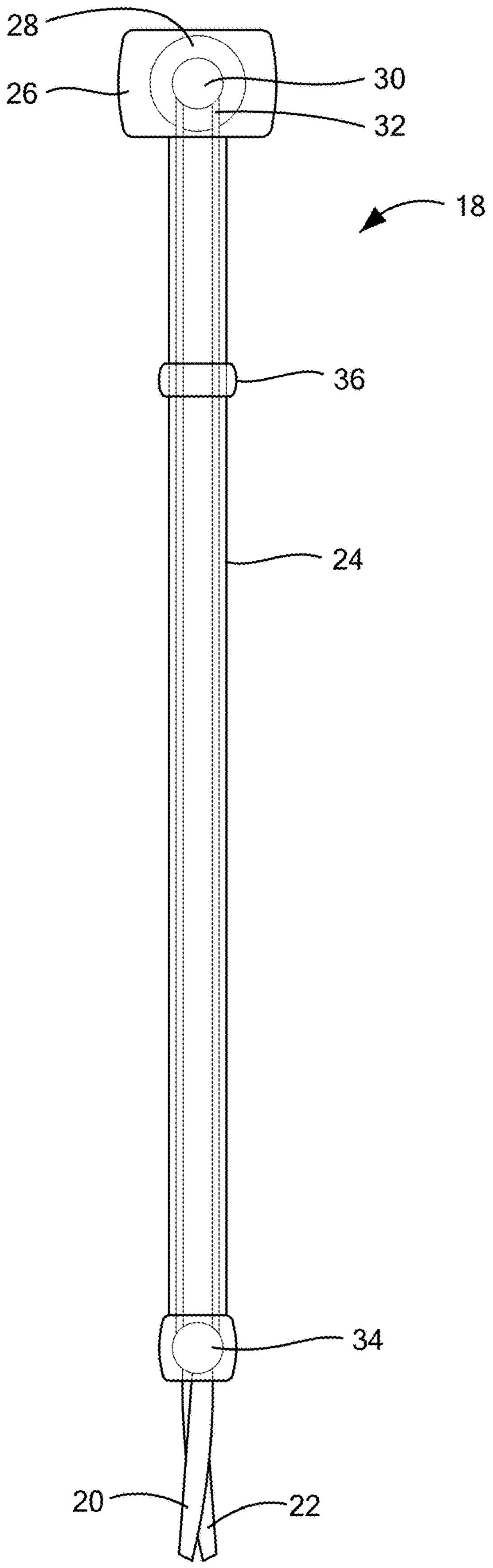
FIG. 2 is a side, schematic view of an incision expander in accordance with the invention.

FIG. 2 illustrates a laparoscopic incision extender 18 of the invention that can be inserted in whole or in part into and through the passage defined by the trocar 12. The incision extender 18 includes one or more cutting blades and a cutting blade control and deployment mechanism or assembly. In the illustrated device, two blades 20 and 22 are shown in a retracted or non-deployed state wherein they are generally axially aligned with a tubular body, hereinafter a tube 24, so they can pass through a trocar because they and the tube have a diameter that is less than the inner diameter of the trocar. The tube 24 houses elements of a blade control and deployment mechanism that includes a housing 26 for a precision motor 28. As described below, the motor 28 provides a controlled rotational force that moves a belt for blade deployment. The motor 28 can be a stepper motor or servo motor capable of precise positional control, programmable speed regulation, and consistent torque delivery under varying load conditions. The housing 26 is both a protective enclosure for the motor 28 and a positioning structure or stop that ensures that the tube 24, and blades 20 and 22 are inserted a selected distance through the trocar 12.

The motor 28 drives a first pulley 30, which is operatively connected to the motor through a coupling mechanism like a drive shaft that ensures reliable power transmission while maintaining precision control. A flexible belt 32 extends from this first pulley 30 through the entire length of the tube 24 to a second pully 34 near the distal end of the tube. The second pulley 34 has an interface with the cutting blades 20 and 22. The cutting blades 20 and 22 are attached to the second pulley 34 so that rotation of the second pulley in one direction by movement of the belt 32, caused by rotation of the first pulley 30, powered by the motor 28, causes the blades to rotate or pivot outward away from the centerline of the tube a selected distance. This dual-blade configuration ensures symmetrical incision extension, addressing one of the significant limitations of single-blade systems that may create asymmetrical or irregular enlargements. The synchronized operation of both cutting blades provides balanced cutting forces and uniform incision geometry, resulting in improved cosmetic outcomes and functional results. The blades are shown as being straight, but could be curved. Also, more than two blades could be included.

The motor 28 can include an interface that allows a surgeon to preset cutting speeds, deployment angles, and blade positioning based on specific procedural requirements and specimen characteristics. Consistent deployment eliminates the variability associated with manual operation, ensuring reproducible results regardless of surgeon experience or fatigue levels. Reduced surgeon fatigue is achieved by eliminating the need for manual force application during the critical blade deployment phase.

Figure 3:
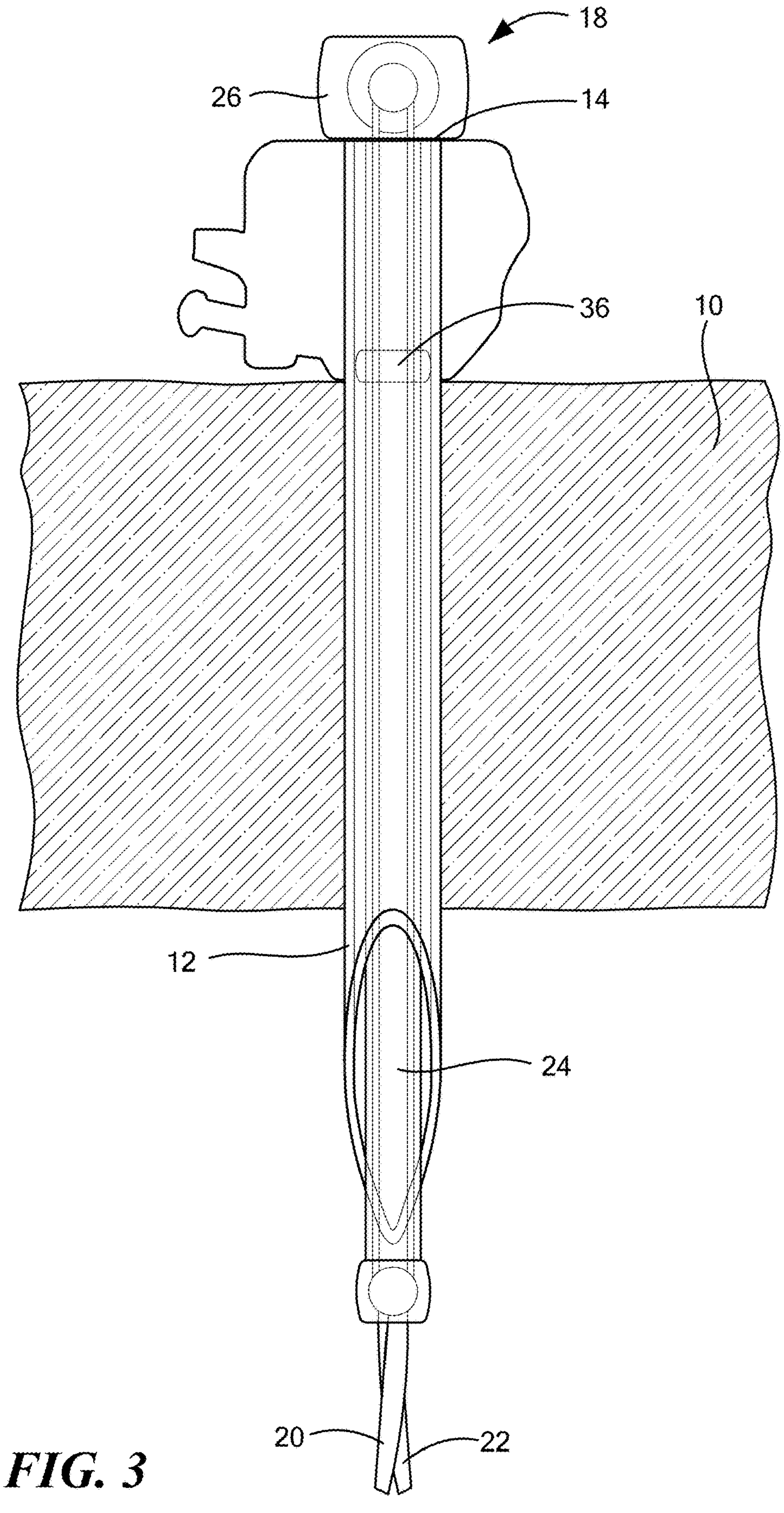
FIG. 3 shows the incision expander of FIG. 2 inserted into the trocar of FIG. 1 with cutting blades in a retracted position.

Referring to FIG. 3, the incision extender 18 is shown inserted into the trocar 12 wherein the housing 26 at the proximal end rests on the proximal end of the trocar. The tube 24 is positioned within the trocar 12 and the blades 20 and 22 extend therefrom. The exterior surface of the tube 24 can be provided with a low-friction biocompatible coating such as PTFE or silicone-based material to reduce insertion force and minimize tissue trauma during withdrawal. One or more positioning elements 36 can be affixed to the exterior of the tube 24 to help stabilize the tube within the trocar 12. The positioning elements 36 can have a thickness as required depending on the outer diameter of the tube 24 and the inner diameter of the trocar 12. In this way, a single “smaller” incision extender 18 can be adapted to snugly fit within trocars having different diameters.

Figure 4:
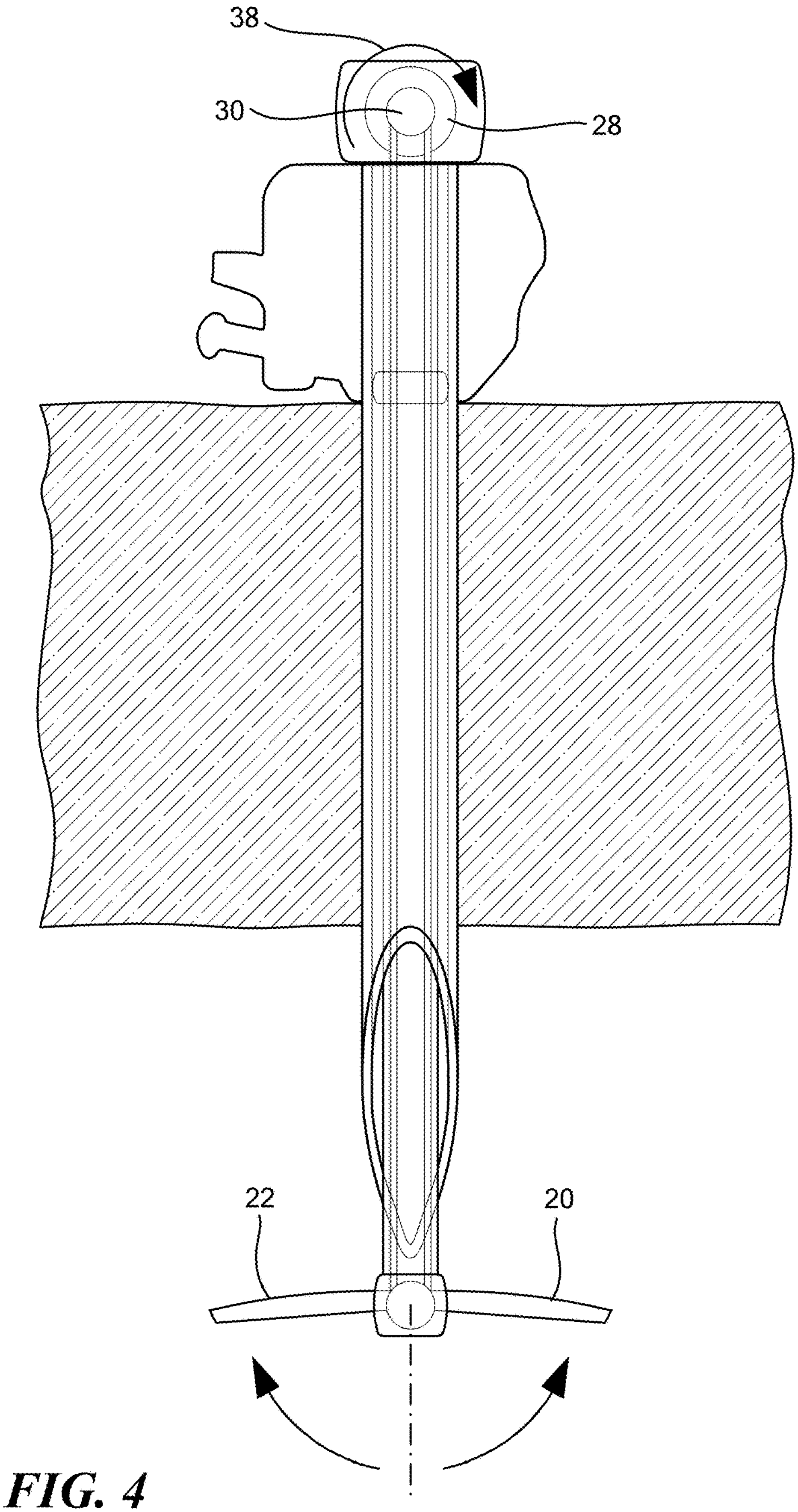
FIG. 4 shows the incision expander of FIG. 2 inserted into the trocar of FIG. 1 with cutting blades in an expanded or cutting position.

FIG. 4 is a view similar to FIG. 3, but in this view the motor 28 has rotated the first pulley 30 as shown by the arrow 38 to move the belt 32 to cause extension of the cutting blades 20 and 22 to place them in position for cutting tissue.

Figure 5:
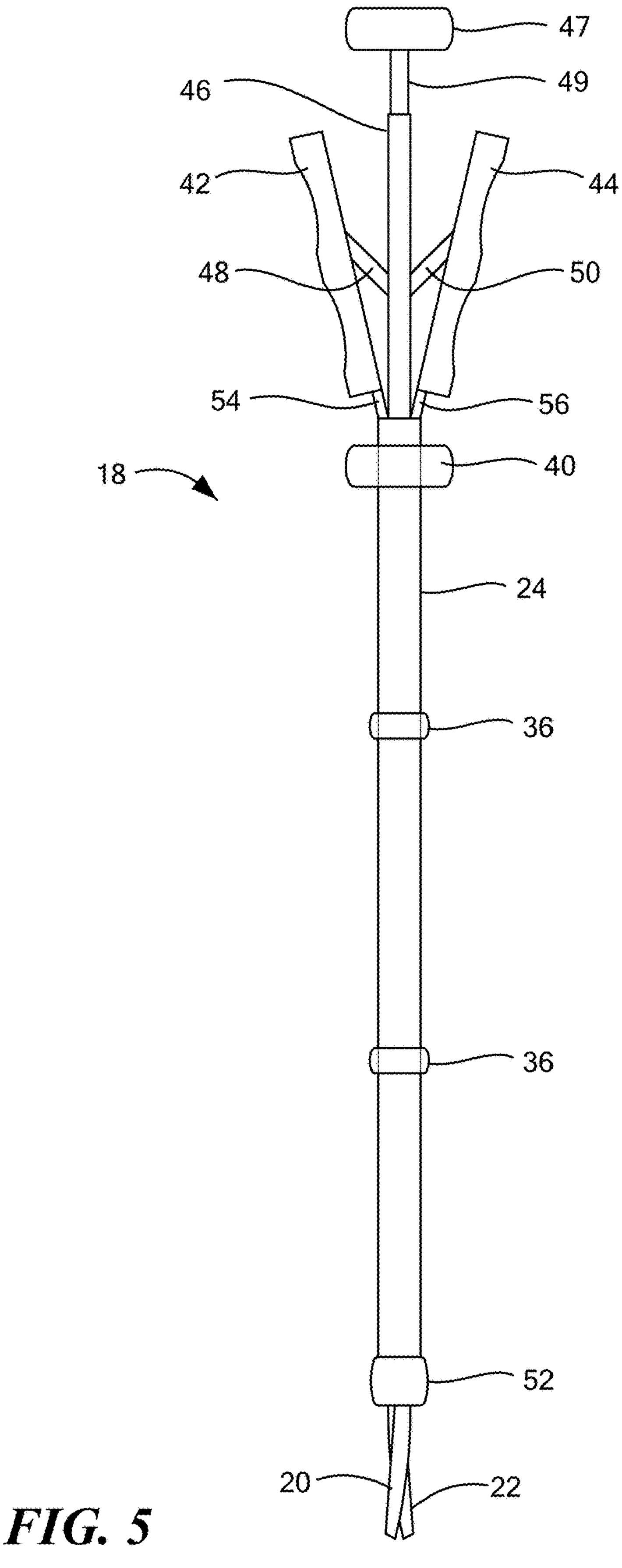
FIG. 5 depicts an embodiment of the incision expander with an alternate blade deployment mechanism with the cutting blades in a retracted position.

Turning now to FIG. 5, another embodiment of the cutting blade deployment mechanism is shown. In this embodiment a manual system provides immediate tactile response and eliminates the need for external power sources during operation. This embodiment utilizes the same basic tube configuration designated as element 1. The tube incorporates positioning elements 36 that maintain proper alignment within the trocar during insertion and operation, ensuring consistent positioning and preventing rotation or displacement that could compromise blade deployment accuracy. A stop mechanism 40 provides positioning feedback and ensures proper depth of insertion within the trocar.

Figure 6:
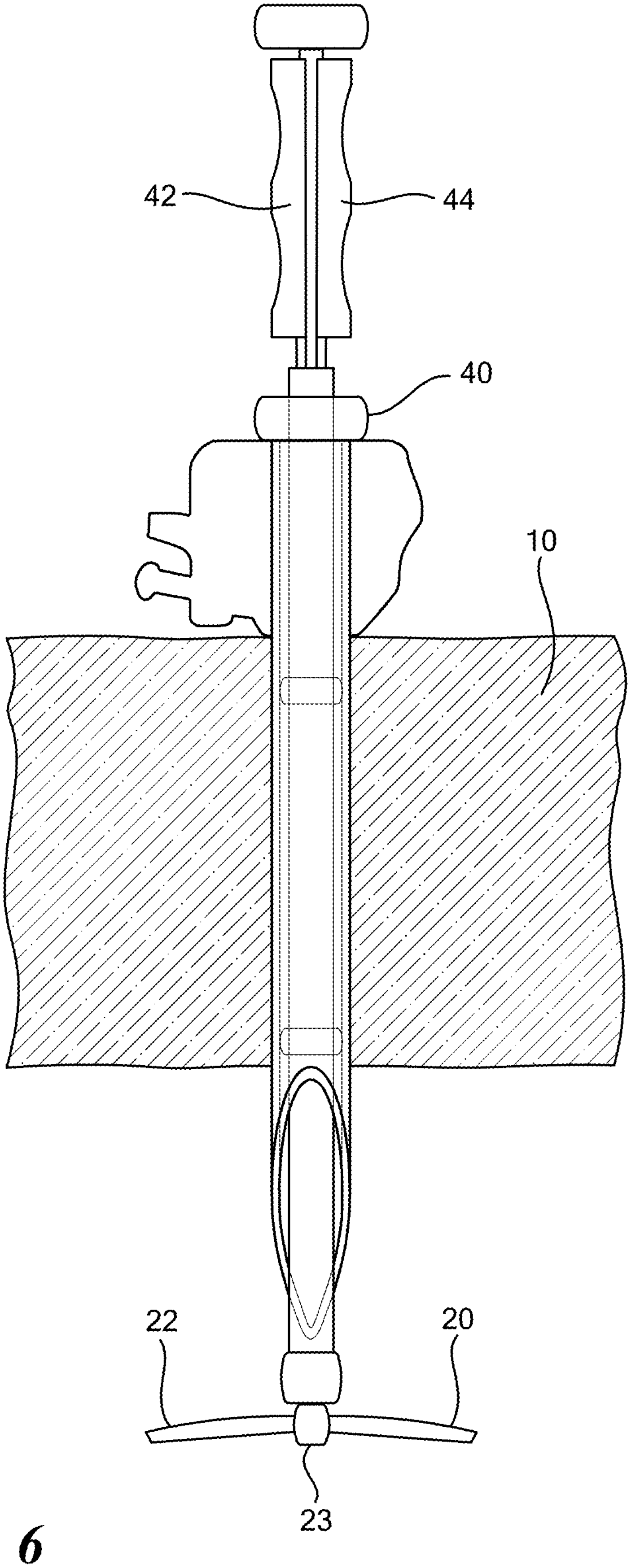
FIG. 6 illustrates the incision expander of FIG. 5 inserted into the trocar of FIG. 1 with the cutting blades in an expanded or cutting position.

First and second handles 42 and 44 respectively are positioned at the proximal end of the incision extender 18. The handles 42 and 44 are connected to a central rod 46 with first and second mechanical linkages 48 and 50. When the handles are pivoted away from the central rod 46, the blades 20 and 22 are in the retracted position. As the handles move together as shown in FIG. 6, the blades 20 and 22 transition to the extended position. As the handles move together, the rod 46 moves down the tube exposing mechanism 23. Mechanism 23 is a spring mechanism which has the blades 20 and 22 linked to it. The spring mechanism 23 is connected through an internal rod 49 that is disposed within the rod 46. The internal rod 49 is connected to a knob 47. When the handles are closed, the spring mechanism 23 is exposed and the blades are free to open. In this state, the knob 47 can be depressed to activate the spring mechanism inside 23. When the spring mechanism is activated, the blades spring open.

Additionally, a spring mechanism 52 can be associated with the rod 46 so that as the handles are closed, the rod is pressed downward to activate the spring mechanism causing the blades to extend. The handles 42 and 44 can be anchored with flexible arms 54 and 56.

Figure 7:
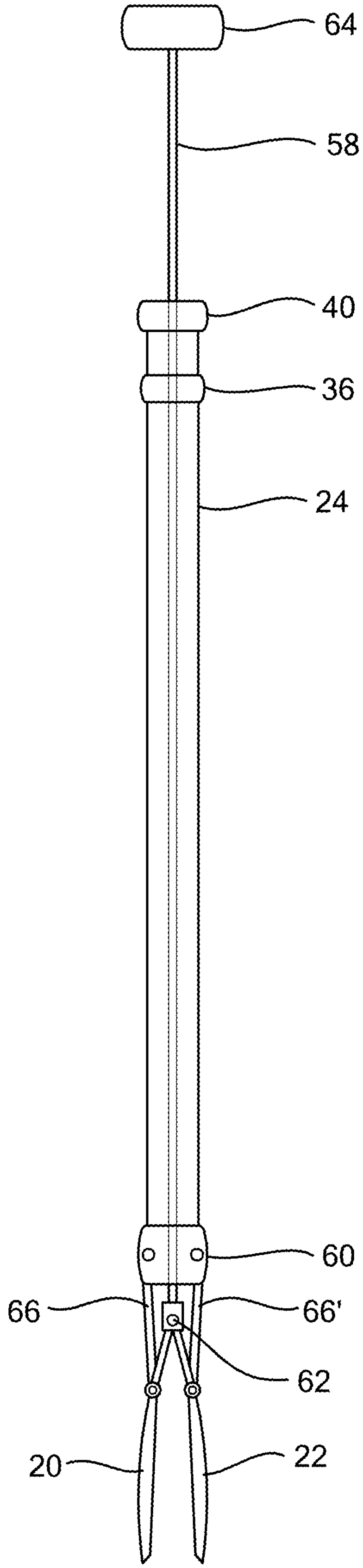
FIG. 7 depicts another embodiment of the incision expander with another embodiment of the blade deployment mechanism with the cutting blades in a retracted position.

Referring now to FIG. 7, a third embodiment of the cutting blade deployment mechanism incorporates a threaded rod system that provides graduated, measurable control over incision widening. The deployment mechanism includes a rod 58 that extends from the proximal end of the tube 24 to the distal region where the rod is threaded and to passes through and engages a threaded ring 60. The rod 58 terminates at a link 62 to which it is secured. The proximal end of the rod 58 engages a knob 64 that facilitates rotation of the rod. The knob 64 can be provided with indicia that identify a rotational position or orientation of the knob with the tube 24. In this and the other embodiments, the rod can also include indicia or a gauge to measure longitudinal movement within the tube 24. As with other embodiments, a positioning element 36 and a stop mechanism 40 are provided. It will be noted in each of the embodiments that the tube 24 is not completely filled with structures and there is ample room to provide for passage or storage of a string for an endobag. Alternatively, a groove can be provided along the length of the tube 24 to allow the string of an endobag to be protected.

As the knob 64 is rotated in one direction the rod 58 moves longitudinally through the tube 24 toward the distal end of the tube. As the knob is rotated in an opposite direction, the rod moves longitudinally through the tube toward the proximal end of the tube. A small, programmable motor (not shown) can be used to rotate the rod to achieve specific deployment parameters based on procedural requirements and surgeon preferences.

Figure 8:
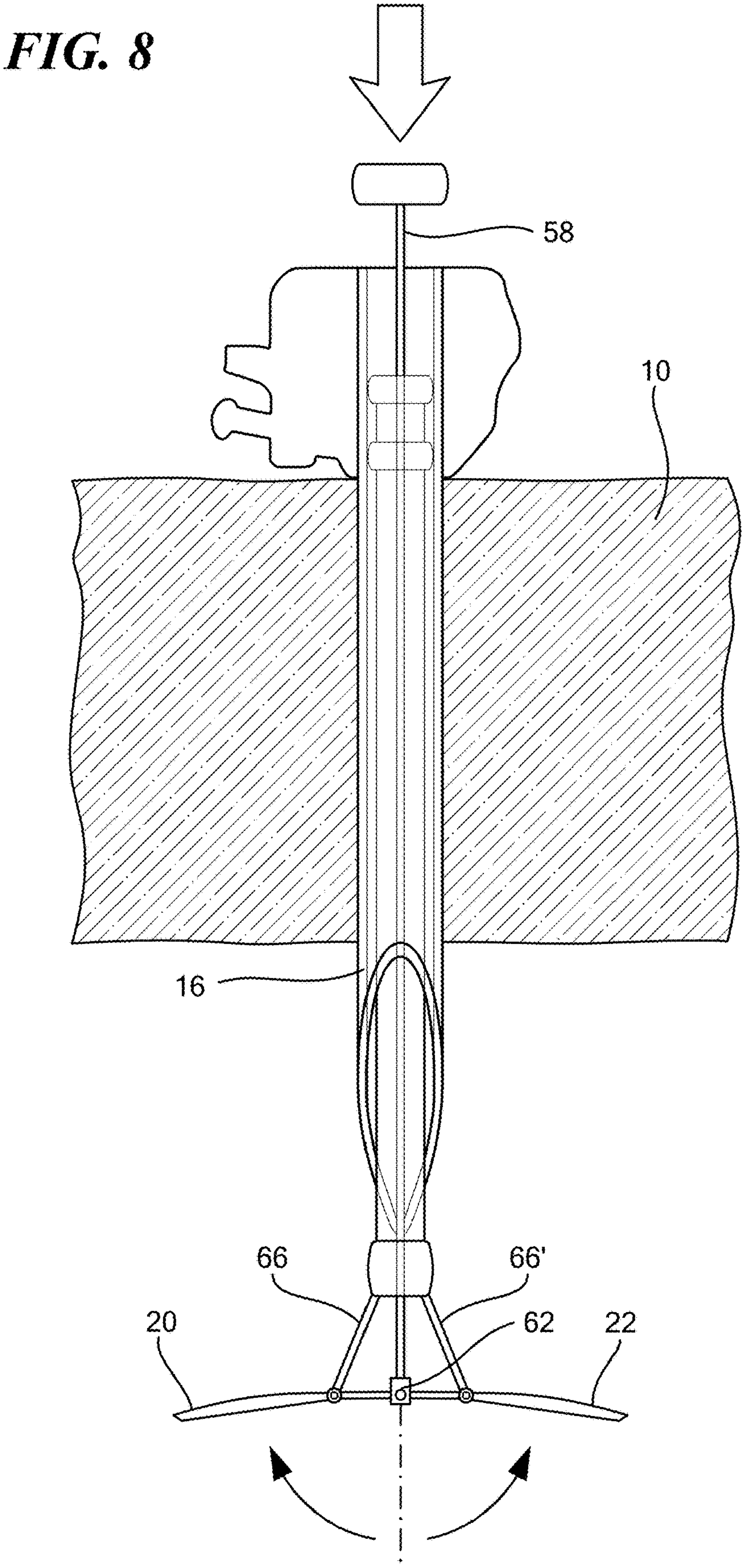
FIG. 8 illustrates the incision expander of FIG. 7 inserted into the trocar of FIG. 1 with the cutting blades in an expanded or cutting position.

As noted above, the distal end of the rod 58 is secured to a link 62 that is joined the cutting blades 20 and 22. As the rod 58 is rotates and moves, the link 62 moves causing the cutting blades 20 and 22 to extend when the rod rotates to move distally and to retract when the rod rotates in the opposite direction and moves proximally. This is shown in FIG. 8. A linkage 66, 66' connects a distal portion of the tube 16 at the threaded ring 60 to an intermediate point on the blades 20 and 22, respectively. The blades can rotate/pivot with respect to the distal end of the linkages at the point identified as a circle (a pin location as described below) when the link 62 moves distally and proximally in response to longitudinal movement of the rod 58. In one embodiment, the blades define a through hole through which a pin is placed to make the connection with the linkages. Thus, the links 66 and 66' can be fastened to the link 60 with pins (as shown in FIG. 7). As noted, the links 66 and 66' can also be fastened on their distal ends to an intermediate point of the blades 20 and 22. The points of attachment are represented as small circles that are the tops of flush-mounted pins placed into holes, wherein the pins allow for rotational movement of the joined elements while also securely joining the elements.

Figure 9:
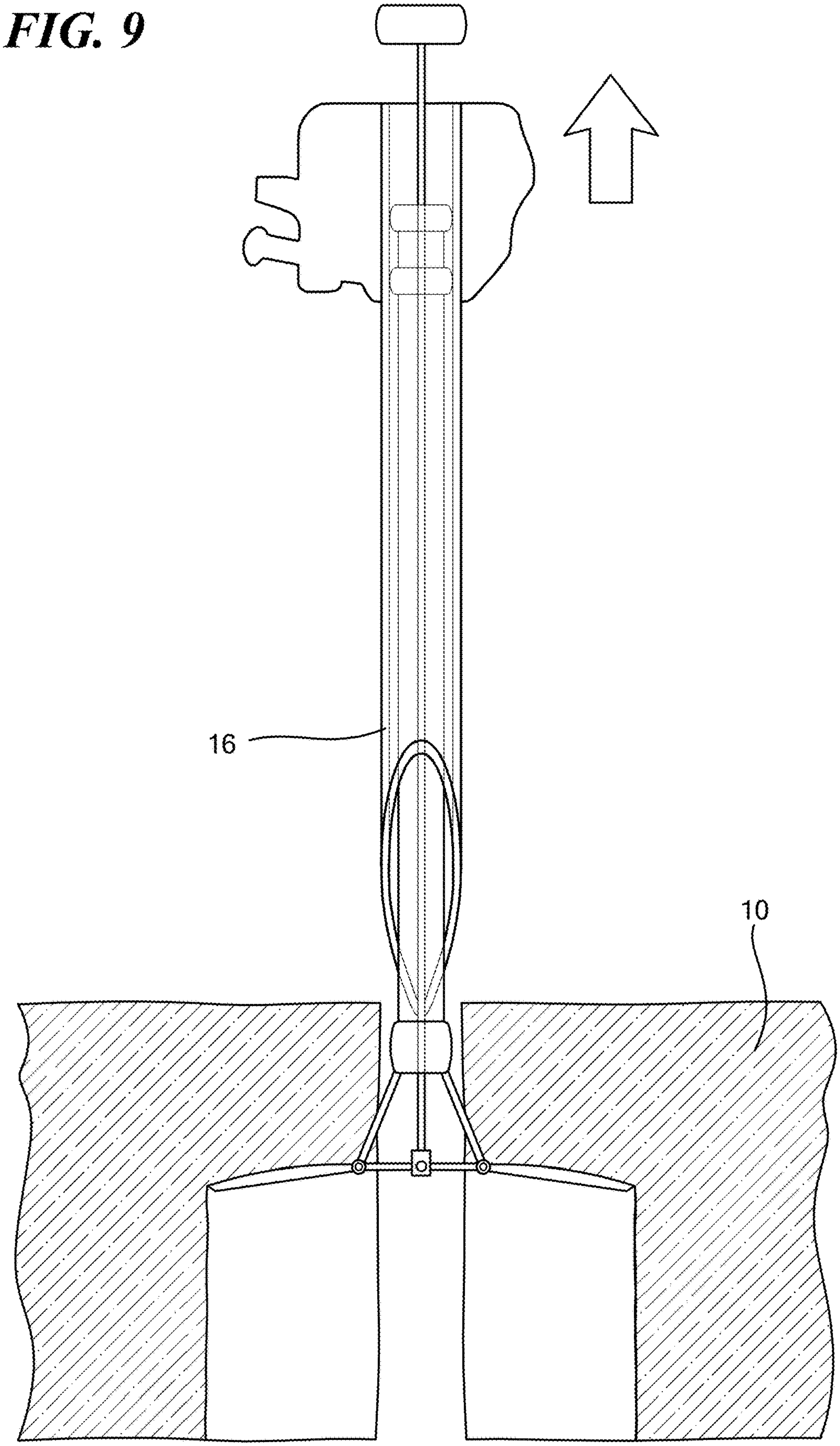
FIG. 9 shows the cutting blades cutting tissue as the trocar and incision expander of FIG. 8 are withdrawn from the body.

FIG. 9 shows the simultaneous withdrawal of the device and the trocar from the abdomen 10 to cause the blades with their sharpened edges facing the tissue to cut through tissue and expand the original laparoscopic incision or puncture.

The operational sequences for all embodiments follow similar patterns while incorporating the unique characteristics of each deployment mechanism. Initial insertion involves introducing the selected device through the trocar until proper positioning is achieved as indicated by the stop mechanism engagement with internal trocar surfaces. The tube must extend sufficiently into the peritoneal cavity to allow complete blade deployment within the body cavity, ensuring that the cutting or retraction action occurs in the appropriate anatomical location.

The entire device may be preassembled as a sterile, single-use cartridge for convenience and infection control. The cartridge may include the tubular body, internal deployment mechanism, and blade assembly in a sealed, sterilized configuration.

The versatility of having multiple embodiments available allows surgeons to select the most appropriate system based on specific procedural requirements, specimen characteristics, and individual preferences. This flexibility represents a significant advancement over single-approach solutions and enables optimization of outcomes across a wide range of laparoscopic procedures and surgical specialties.

In an exemplary method of using the device, an original incision made to place a laparoscope is extended by inserting a device as described above through a trocar/casing tube such that the cutting blades are positioned within a body cavity beyond multiple tissue layers. The deployment mechanism is activated to deploy the blades from a retracted to an extended position while maintaining laparoscopic visualization. The blades are maintained in extended positions with their cutting edges facing the tissue and the proximal end of the device, and the device and the trocar are simultaneously removed from the body while the blades are extended, thereby cutting or retracting through peritoneum, facia and skin to enlarge the trocar incision. A specimen or mass is then removed through the enlarged incision. Additionally or alternatively, the enlarged incision can provide improved access to the surgical field.

It will be appreciated by persons skilled in the art that the present invention is not limited to what has been particularly shown and described herein above. In addition, unless mention was made above to the contrary, it should be noted that all the accompanying drawings are not to scale. A variety of modifications and variations are possible considering the above teachings without departing from the scope and spirit of the invention, which is limited only by the following claims.

What is claimed is:

1. A surgical instrument for insertion through a laparoscopic trocar/casing tube, the instrument comprising:

a housing tube sized for passage through the trocar/casing tube;

a deployment assembly at least partially disposed within the housing tube wherein the deployment assembly comprises:

a rod disposed longitudinally within the housing tube, the rod having a threaded portion at a distal end;

a threaded ring at a distal portion of the housing tube, the threaded ring engaged with the threaded portion of the rod, wherein rotation of the rod causes longitudinal movement of the rod through the threaded ring;

a link secured to the distal end of the rod and movable longitudinally with the rod;

a first set of cutting blade-links, each cutting blade-link of the first set having a proximal end connected to the threaded ring at a first connection point and a distal end, wherein the cutting blade-links of the first set comprise cutting edges along radially outer portions;

a second set of cutting blade-links, each cutting blade-link of the second set having a proximal end joined to the link at a second connection point and an intermediate portion joined to the distal end of a respective cutting blade-link of the first set at a third connection point, wherein the cutting blade-links of the second set comprise cutting edges along radially outer portions;

wherein the first, second, and third connection points comprise pins allowing rotational movement;

wherein rotation of the rod causes the link to move longitudinally, thereby causing the first set of cutting blade-links to pivot radially outward about the first connection point while the second set of cutting blade-links simultaneously pivot radially outward about the second connection point; and at least one cutting blade coupled to the deployment assembly, the at least one cutting blade having a sharpened cutting edge, and the at least one cutting blade movable between a retracted position within a perimeter diameter defined by the housing tube and an extended position projecting beyond the perimeter diameter, wherein the deployment assembly is configured to deploy the at least one cutting blade while the housing tube remains positioned within the trocar/ casing tube such that the at least one cutting blade extends radially outward beyond an outer perimeter of the trocar/casing tube, and wherein the at least one cutting blade is configured to cut tissue during simultaneous withdrawal of both the instrument and the trocar/casing tube from a body cavity.

2. The instrument of claim 1, further comprising a motor connected to the rod to rotate the rod relative to the housing tube, wherein rotation of the rod by the motor causes longitudinal movement of the rod through the threaded ring.

3. The surgical instrument of claim 1, further comprising a positioning element disposed on an exterior surface of the housing tube to separate the housing tube from an interior wall of the trocar, wherein the positioning element has a thickness selected based on an inner diameter of the trocar to provide a snug fit of the housing tube within the trocar.

4. The surgical instrument of claim 1, wherein the housing tube has an exterior diameter between 5 millimeters and 15 millimeters, and wherein the housing tube is configured to fit within a trocar having a corresponding inner diameter between 5 millimeters and 15 millimeters.

5. The surgical instrument of claim 1, wherein the at least one cutting blade extends and retracts by pivoting, and wherein the at least one cutting blade pivots through a range of motion from a position substantially aligned with a longitudinal axis of the housing tube in the retracted position to a position extending radially outward at an angle to the longitudinal axis in the extended position.

6. The surgical instrument of claim 1, wherein the housing tube has a proximal end and a distal end, wherein the at least one cutting blade is at the distal end, and wherein the sharpened cutting edge faces the proximal end when the at least one cutting blade is in the extended position, and wherein the sharpened cutting edge is oriented to cut tissue as the instrument and the trocar/casing tube are simultaneously withdrawn proximally from the body cavity.

7. The surgical instrument of claim 1, wherein all cutting blade-links of both the first set and the second set comprise cutting edges configured to cut tissue when extended radially outward.

* * * * *